US010039528B1

(12) United States Patent
Lee

(10) Patent No.: US 10,039,528 B1
(45) Date of Patent: **\*Aug. 7, 2018**

(54) SYSTEMS, DEVICES, AND METHODS FOR INTEGRATED PATIENT SERVICE CENTER

(71) Applicant: Theranos IP Company, LLC, Newark, CA (US)

(72) Inventor: Gayle Lee, Palo Alto, CA (US)

(73) Assignee: Theranos IP Company, LLC, Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/404,361

(22) Filed: Jan. 12, 2017

Related U.S. Application Data

(63) Continuation of application No. 15/160,936, filed on May 20, 2016, now Pat. No. 9,572,550, which is a continuation of application No. 14/214,599, filed on Mar. 14, 2014, now Pat. No. 9,538,992.

(60) Provisional application No. 61/852,484, filed on Mar. 15, 2013.

(51) Int. Cl.
*A61B 10/00* (2006.01)
*A61B 5/15* (2006.01)
*G01N 1/44* (2006.01)

(52) U.S. Cl.
CPC .... *A61B 10/0096* (2013.01); *A61B 5/150076* (2013.01); *G01N 1/44* (2013.01)

(58) Field of Classification Search
CPC ............ A61B 10/0045; A61B 10/0096; A61B 5/150076; A61B 5/6889; B65D 55/02
See application file for complete search history.

(56) References Cited

U.S. PATENT DOCUMENTS

| | | | |
|---|---|---|---|
| 6,403,897 B1* | 6/2002 | Bluth | A61B 5/0002 128/920 |
| 6,692,436 B1* | 2/2004 | Bluth | A61B 5/0002 128/904 |
| 9,538,992 B1 | 1/2017 | Lee | |
| 9,572,550 B1 | 2/2017 | Lee | |
| 2003/0120384 A1 | 6/2003 | Haitin et al. | |
| 2007/0073113 A1* | 3/2007 | Squilla | A61B 5/00 600/300 |
| 2007/0215018 A1* | 9/2007 | Faries, Jr. | E05B 47/026 109/23 |

(Continued)

OTHER PUBLICATIONS

Notice of Allowance dated Oct. 7, 2016 for U.S. Appl. No. 15/160,936.

(Continued)

*Primary Examiner* — Francis Gray

(57) ABSTRACT

Bodily fluid sample collection systems, devices, and method are provided. The device may comprise a first portion comprising at least a sample collection channel configured to draw the fluid sample into the sample collection channel via a first type of motive force. The sample collection device may include a second portion comprising a sample container for receiving the bodily fluid sample collected in the sample collection channel, the sample container operably engageable to be in fluid communication with the collection channel, whereupon when fluid communication is established, the container provides a second motive force different from the first motive force to move a majority of the bodily fluid sample from the channel into the container.

19 Claims, 8 Drawing Sheets

(56) References Cited

U.S. PATENT DOCUMENTS

| | | | |
|---|---|---|---|
| 2007/0228680 A1 | 10/2007 | Reppert et al. | |
| 2009/0241177 A1* | 9/2009 | Bluth | A61B 5/02055 |
| | | | 726/7 |
| 2010/0268380 A1* | 10/2010 | Waugh | G07F 11/44 |
| | | | 700/239 |
| 2012/0004770 A1* | 1/2012 | Ooyen | G06F 19/3462 |
| | | | 700/235 |
| 2012/0012606 A1* | 1/2012 | Longley | G07F 11/58 |
| | | | 221/92 |
| 2012/0179479 A1* | 7/2012 | Waterson | G06F 19/3418 |
| | | | 705/2 |
| 2012/0253837 A1* | 10/2012 | Cashman | E04H 1/1205 |
| | | | 705/2 |
| 2013/0092700 A1* | 4/2013 | Braunstein | G07F 9/006 |
| | | | 221/13 |

OTHER PUBLICATIONS

Notice of Allowance dated Mar. 15, 2016 for U.S. Appl. No. 14/214,599.

\* cited by examiner

SYSTEMS, DEVICES, AND METHODS FOR INTEGRATED PATIENT SERVICE CENTER

BACKGROUND

A blood sample for use in laboratory testing is often obtained by way of venipuncture, which typically involves inserting a hypodermic needle into a vein on the subject. Blood extracted by the hypodermic needle may be drawn directly into a syringe or into one or more sealed vials for subsequent processing. When a venipuncture may be difficult or impractical such as on a newborn infant, a non-venous puncture such as a heel stick or other alternate site puncture may be used to extract a blood sample for testing. After the blood sample is collected, the extracted sample is typically packaged and transferred to a processing center for analysis.

Unfortunately, conventional sample collection and testing techniques of bodily fluid samples has drawbacks. One of them is the lack of easily accessible sampling sites and patient service centers in locations that are more readily accessible to the patient.

SUMMARY

At least some of disadvantages associated with the prior art are overcome by at least some or all of the embodiments described in this disclosure. Although the embodiments herein are typically described in the context of obtaining a blood sample, it should be understood that the embodiments herein are not limited to blood samples and can also be adapted to acquire other fluid(s) or bodily sample(s) for analysis.

In one embodiment, an integrated patient service center is provided comprising: a user accommodation section adapted to locate a user in at least one position that enables an interaction between the station and the user; a user interface adapted to permit a user to input data relevant to the user; wherein said at least one position enables the user to position a portion of their body onto a work surface for obtaining patient service; a secured, temperature controlled sample storage location that is configured to be accessible through a first opening; and a lockable cover for securing the a user interface but not the sample storage location.

In another embodiment, an integrated patient service center is provided comprising a user accommodation section adapted to locate a user in at least one position that enables an interaction between the station and the user; a user interface adapted to permit a user to input data relevant to the user; wherein said at least one position enables the user to position a portion of their body onto a work surface for obtaining patient service; a secured, temperature controlled sample storage location that is configured to be accessible through a first opening and a second opening, wherein a key, code, or structure to open one opening does not open the other opening.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DESCRIPTION OF THE SPECIFIC EMBODIMENTS

Figure 1:
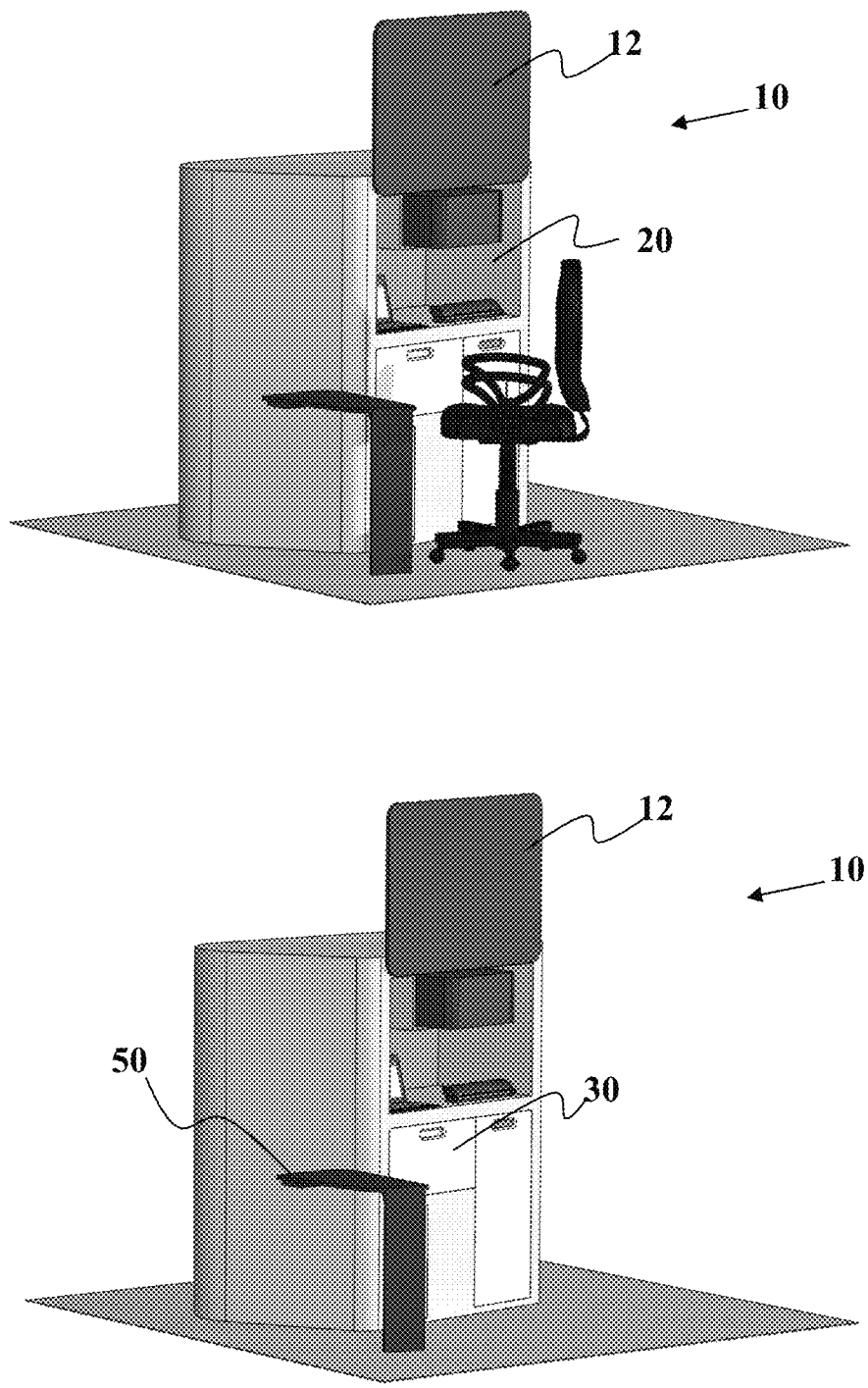
FIGS. 1-8 show views of integrated patient service center according to embodiments as described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection well, this means that the sample collection well may or may not be present, and, thus, the description includes both structures wherein a device possesses the sample collection well and structures wherein sample collection well is not present.

By way of non-limiting example, one embodiment of an integrated patient service center herein provides a location for a practitioner to sit and obtain a bodily fluid or other sample from the patient. A work surface such as a table is provided so that a patient has a surface on which they can position the target site on the subject to allow for sampling. The work surface can have one or more thermal controlled sites wherein the temperature of the target site on the patient may be brought to a desired temperature. By way of example and not limitation, one embodiment may heat a finger or other target site to improve blood flow and thus blood yield from a fingerstick. In one embodiment, the temperature is sufficient to increase blood flow to yield 120 uL of sample. In one embodiment, the temperature is sufficient to increase blood flow to yield 130 uL of sample. In one embodiment, the temperature is sufficient to increase blood flow to yield 140 uL of sample. In one embodiment, the temperature is sufficient to increase blood flow to yield 150 uL of sample. Optionally, the thermal controlled site is a shaped surface is contoured to match that of the target site on a patient.

Optionally, the integrated patient service center has an integrated table with a heater in it for finger warming as a replacement/alternative for/to our finger warmers. In one embodiment, that table can have the biohazard bin built in and is at optimal height for facilitating the flow of gravity in the finger as droplets form. It is designed for a technician and patient to be sitting together. The table may optionally go into a treatment with an integrated passthrough window specially designed to transfer urine into the blood collection area and into devices.

In one non-limiting example, the integrated patient service center may be an indoor unit. The integrated patient service center may be permanent, but mobile. The integrated patient service center may be configure so that one person at the unit, providing service to another person. The integrated patient service center may be 30×48×52" approximately, err on the side of taller and skinnier.

The integrated patient service center may have security features. The integrated patient service center may be a lockable whole unit. The integrated patient service center may be have a lockable individual drawer unit for after-hours access. The integrated patient service center may be have a lock for electronics in the unit.

The integrated patient service center may be secured during movement. The integrated patient service center may be moveable but stable when locked. The integrated patient service center may have wheels, and maneuverable, but can lock stably into place once in position. The integrated patient service center may have a table that is sturdy, able to be able to carry the weight of 2 people's arms resting on it.

The integrated patient service center may have electrical power to it. The integrated patient service center may have a power strip hidden internally, only have single protruding cable—rest of cables out of sight. The integrated patient service center may have 5-7 electronic devices to be connected, all in main unit (not on side table). The integrated patient service center may have 15-20 Amp out.

The integrated patient service center may be configured to be versatile. The integrated patient service center may have table/workspaces that fold out at least one off the side of the unit and one in the front. The integrated patient service center may have possibly adjustable heights for tables.

The integrated patient service center may be easily cleanable. The integrated patient service center may be easily cleanable surface especially the side table. The integrated patient service center may have FDA/food handling quality for the side table. The integrated patient service center may configured to stay looking clean with use. The integrated patient service center may be configure have a screen or create some space and provide some privacy.

In one embodiment, the integrated patient service center may be configured for 2 people sitting on standard chairs. The integrated patient service center may be have some small quantity of cleaning supplies for the station: surface wipes, hand sanitizer etc. The integrated patient service center may have areas for holding some small quantity of office supplies. The integrated patient service center may have a 3 gallon bin—215×150×450 mm, 2 lb. The integrated patient service center may have a small trash bin 7-13 gallons approx. The integrated patient service center may have a small storage area. The integrated patient service center may have a small storage area for personal items— lockable.

Usage Scenarios:

Case 1: there would already be a counter/check-in place before people are directed to the integrated patient service center.

Case 2: The integrated patient service center would be located within the larger retail area and directly come up to it.

In one embodiment, there will be a privacy screen (separate, about person height) that will be drawn around the integrated patient service center during the procedure, and removed the rest of the time.

Optionally, if parts of the integrated patient service center can pop up above the screen height, that would allow for branding visibility even when the screen is drawn.

Optionally, in all cases the integrated patient service center will be pushed up with the back against the wall, i.e. when the technician is sitting facing the integrated patient service center, they will be facing the wall.

Optionally, the technician may not necessarily be sitting facing the integrated patient service center the whole day though.

Optionally, the back of the integrated patient service center should be fairly flat, and this would affect the overall shape.

Optionally, possibility of changing, since store layouts might change over time.

Optionally, some cases the integrated patient service center might be in a corner.

Optionally, side table, ideally adjustable height with just a little range, maybe a few inches. Chairs that the people will sit on are probably adjustable too. Optionally, ideally can translate and rotate.

Optionally, if the table could come towards you, and one could rotate about the corner, for maximum customizability. The white wireframe 'table' in the mock up is too big right now but a customer needs to fit between the potential back wall and the table, no matter how big or small the customer, and to be able to get in and out easily.

Optionally, the table is mountable on either sides of the integrated patient service center, so that the procedure could take place on either side. Possibly having two tables, one on each side. Optionally, one should still be able to reach across to access a drawer on the other side of the integrated patient service center while at the side table (the footprint constraint already takes care of that, judging from the user tests). Optionally, one could have separate support leg(s) as long as things can be folded away/compact when not in use.

As seen in FIGS. 1 to 8, some common items in the integrated patient service center include but are not limited to printer, touchscreen monitor or non-touch monitor, keyboard tray, keyboard, mouse, USB Wifi Dongle, Power Strip/Surge Protector, Scanner, Collection Table(s), Refrigerator, Refrigerator Thermometer, Supply Cabinet/Drawer(s), Wifi Hotspot.

One embodiment may have a table that fold out to sides and middle, 24-28" high, imagine children's school desk, may be value in having adjustable height, needs to bear weight. Optionally, the patient service center has sharps container, biohazard bin, lancets, BCD, alcohol swabs, gauze, bandaid, pens, gloves, mask, stamp (PROCESSED) or other office supply.

Referring now to FIG. 1, this embodiment shows an integrated patient service center 10 that has a lockable screen or structure 12 that moves from a first position to a second position to close the opening 20 that allows access to the monitor, scanner, and other electronics. The controlled temperature storage unit 30 is provided that is lockable for storage of fluid samples obtained from the patient.

Figure 2:
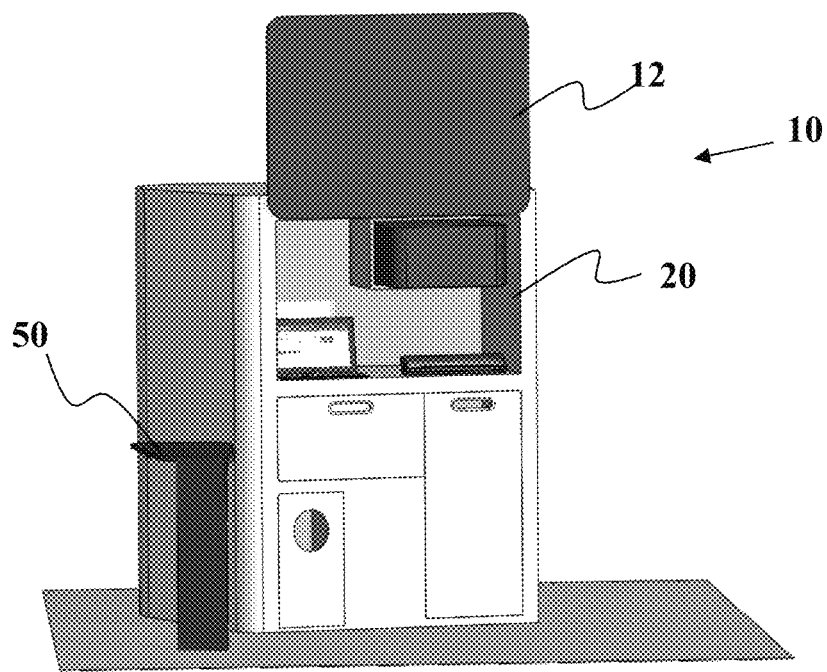
Figure 2:
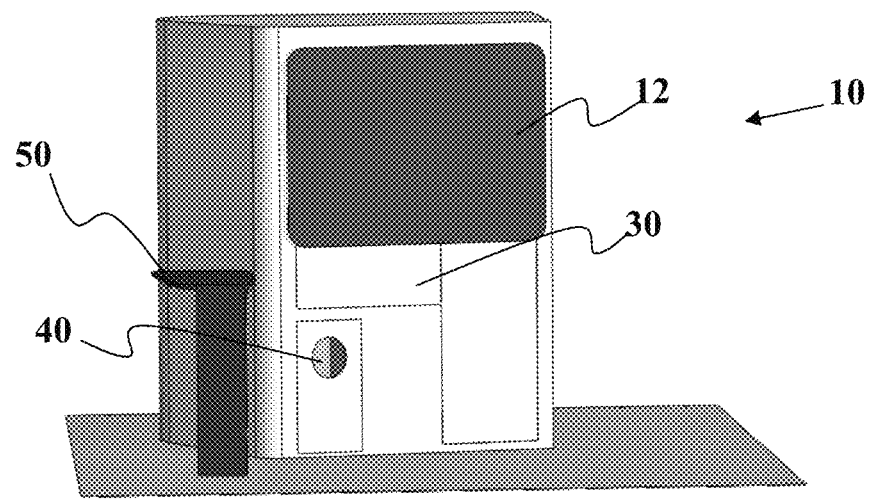

FIG. 2 shows that lockable screen or structure 12 is movable to cover opening 20. A sharps container or trash receptacle 40 is shown in FIG. 2.

Figure 3:
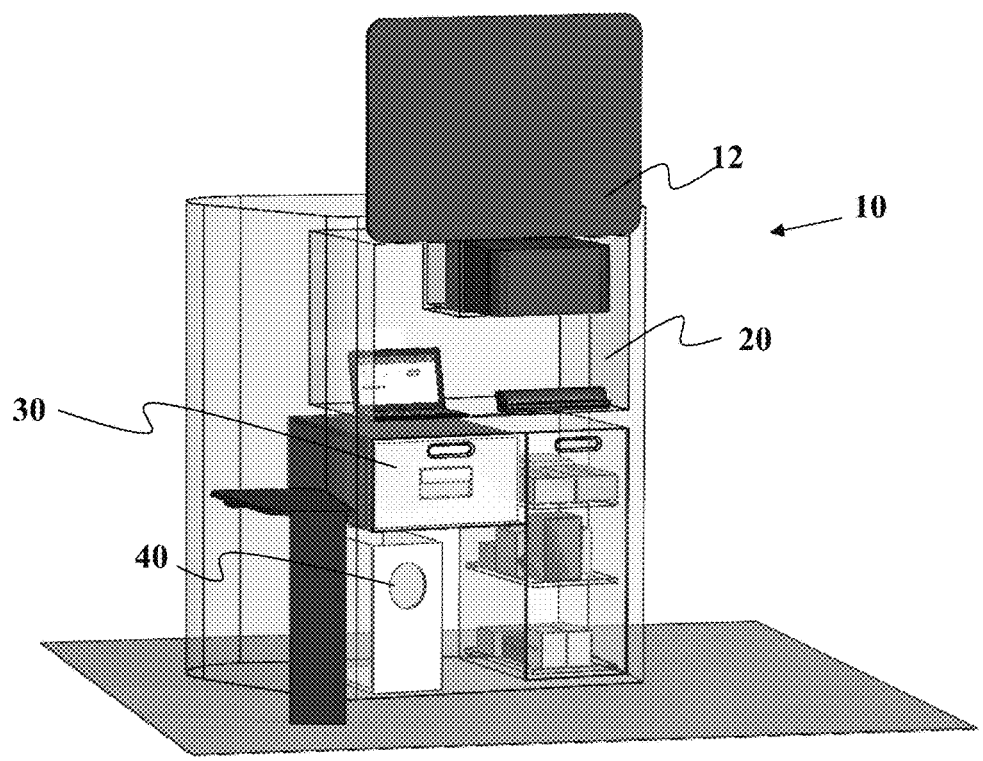

FIG. 3 is a transparent view showing the various component inside an integrated patient service center. It should be understood that the storage unit 30 that is temperature controlled is not covered by the structure 12 when the structure is closed. This allows for the samples in the storage unit 30 to be accessed without have to give access to all of the unit. Optionally, some embodiment may have a second door on the side to allow for access into the storage unit 30. Optionally, some embodiment may have a second door on the back of the center 10 to allow for access into the storage unit 30.

Figure 4:
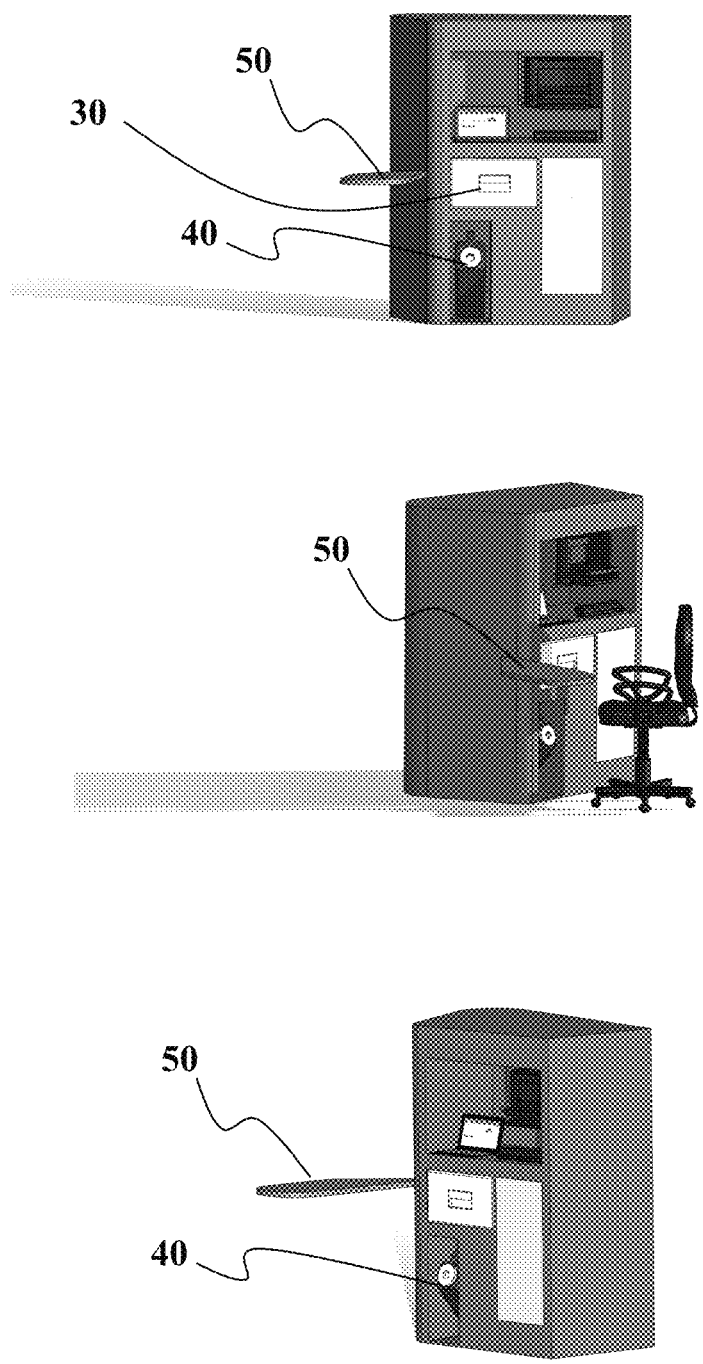

FIG. 4 shows yet another embodiment, wherein table or work surface 50 is movable.

Figure 5:
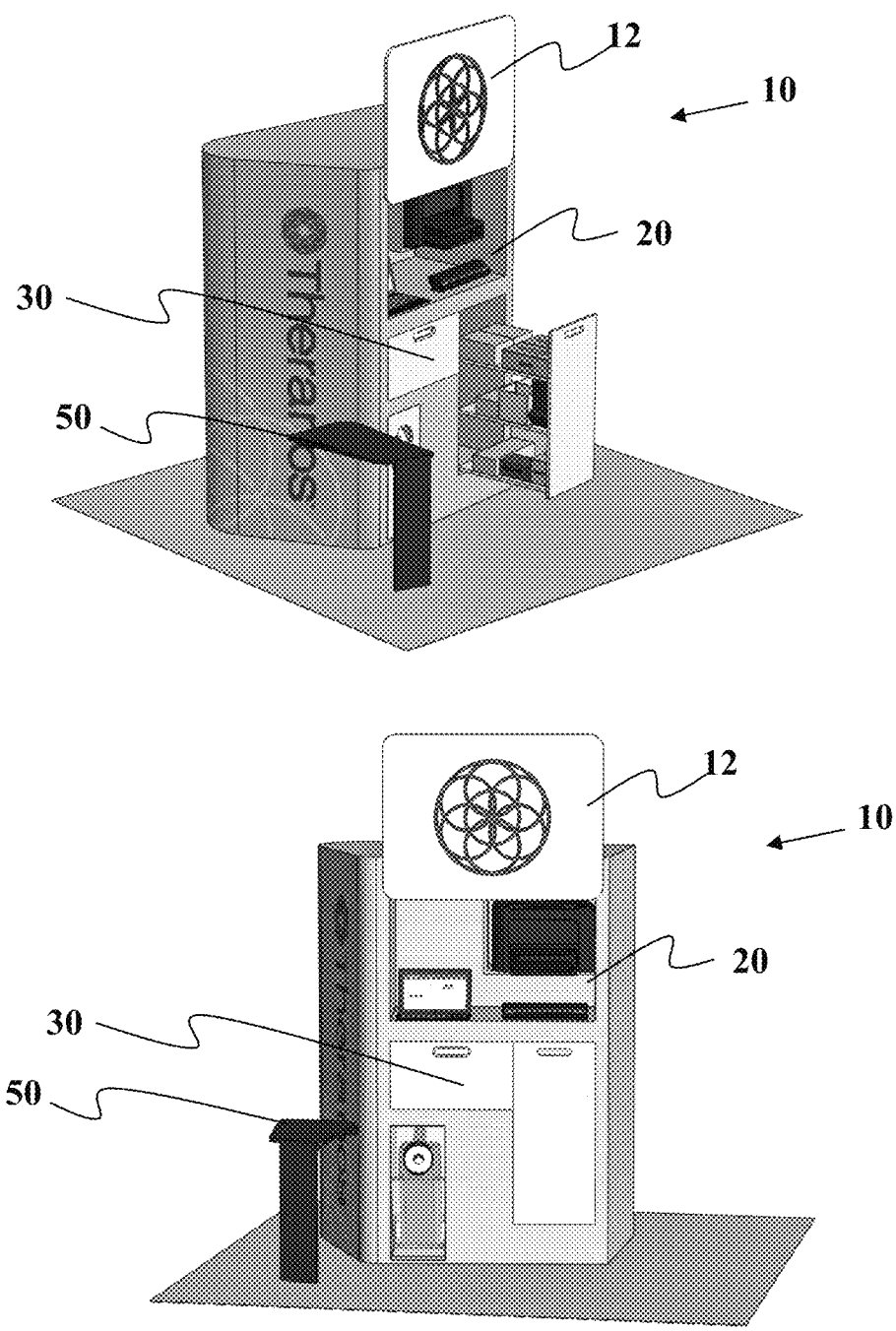
Figure 6:
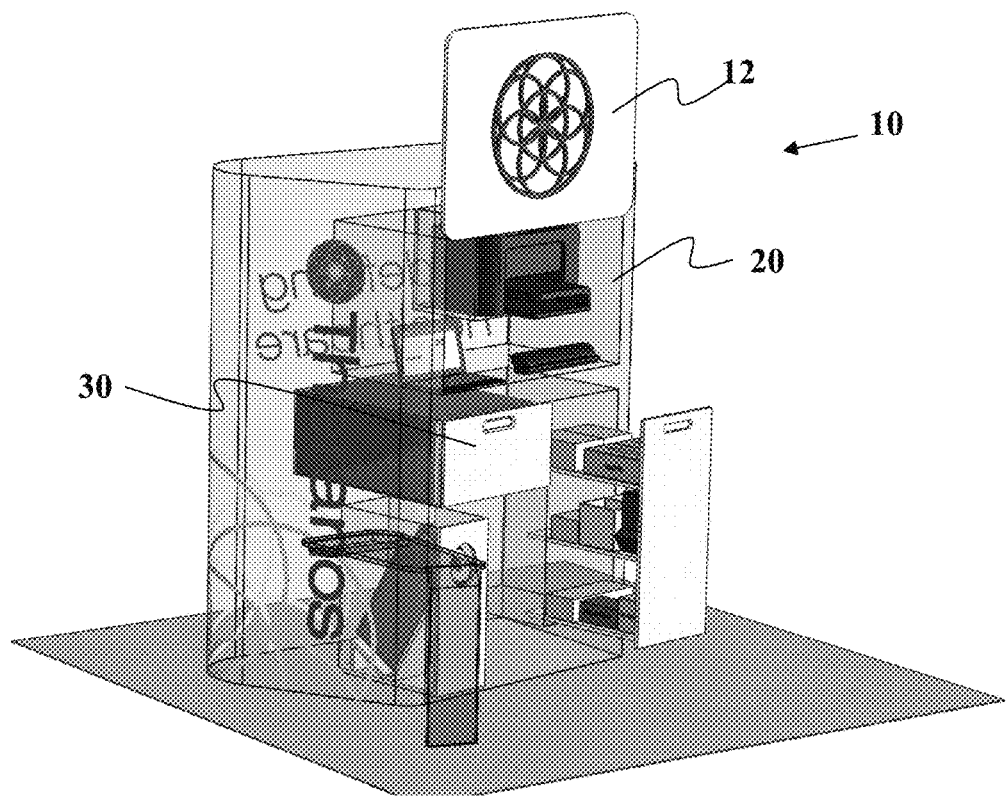

FIGS. 5 and 6 show various views of an integrated patient service center similar to those previously described herein.

Figure 7:
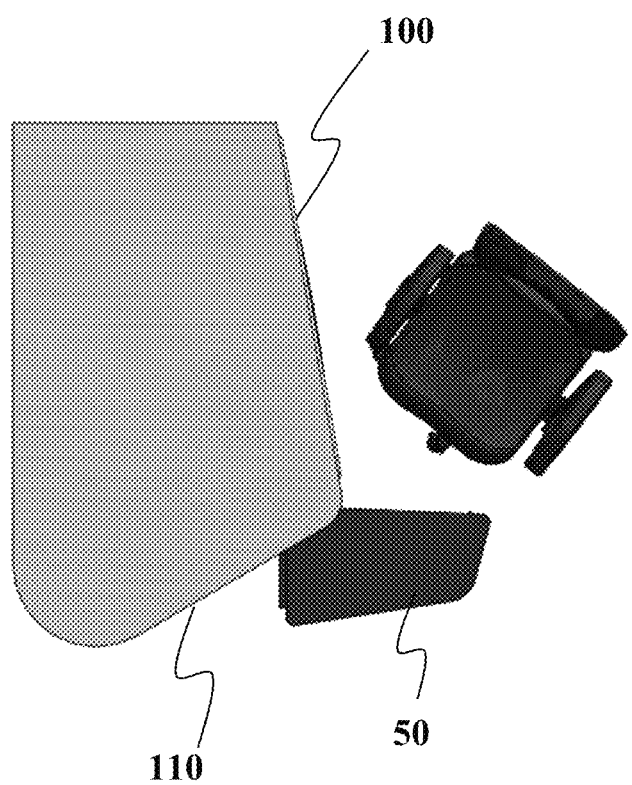
Figure 8:
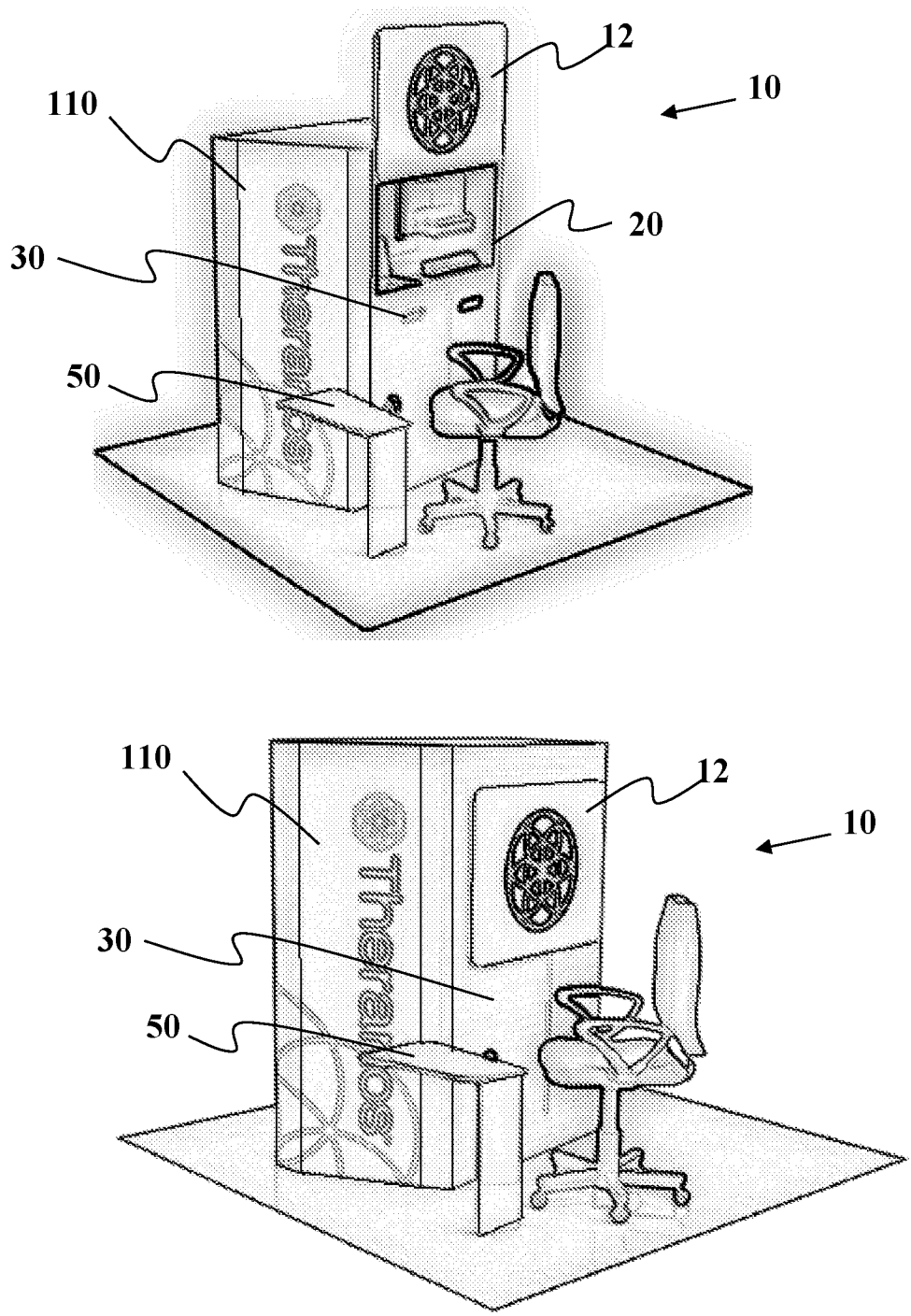

As seen in FIG. 7, the top down plan view shows that the shape of the service center 10 can be configured preferentially direct one portion 100 away from publically viewable areas to provide some more privacy as to information being shown on the any computer monitor. It can also be positioned to enable a user to see information in the service center 10 and be facing somewhat towards the patient who will be near the work surface 50. It also provides for a larger surface 110 to provide for signage or other display information.

While the teachings has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, the table may have thermal control areas to increase blood flow to the target area and thus increase the speed with which sufficient blood or other bodily fluid can be drawn from the subject. The heating is used to bring the target tissue to about 40 C to 50 C. Optionally, the heat brings target tissue to a temperature range of about 44 to 47 C.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes: in U.S. Provisional Patent Application No. 61/435,250, filed Jan. 21, 2011 ("SYSTEMS AND METHODS FOR SAMPLE USE MAXIMIZATION"), and U.S. Patent Publication No. 2009/0088336 ("MODULAR POINT-OF-CARE DEVICES, SYSTEMS, AND USES THEREOF"). The following applications are fully incorporated herein by reference for all purposes: U.S. Pat. No. 8,088,593; U.S. Pat. No. 8,380,541; U.S. patent application Ser. No. 13/769,798, filed Feb. 18, 2013; U.S. patent application Ser. No. 13/769,779, filed Feb. 18, 2013; U.S. Pat. App. Ser. No. 61/766,113 filed Feb. 18, 2013, U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, U.S. Patent Application Ser. No. 61/786,351 filed Mar. 15, 2013, U.S. Patent Application Ser. No. 61/697,797 filed Sep. 6, 2012, U.S. Patent Application Ser. No. 61/852,484 filed Mar. 15, 2013, and U.S. Patent Application Ser. No. 61/733,886 filed Dec. 5, 2012, the disclosures of which patents and patent applications are all hereby incorporated by reference in their entireties for all purposes.

While the above is a complete description of the preferred embodiment as described herein, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013 Theranos, Inc.

What is claimed is:

1. An integrated patient service center unit for use with a user and a user interface, the unit comprising:
   a station having a lockable cover securing at least one portion of the station;
   a user accommodation section defined by the station and adapted to enable an interaction between the station and the user;
   a user interface holder adapted to support a user interface to permit the user to input data, wherein the lockable cover is configured for securing the user interface and the user interface holder;
   a refrigerated, temperature controlled sample storage location that is configured to be accessible through a first opening; and
   a separate lockable access panel for the sample storage location, separate from the lockable cover.

2. The integrated patient service center of claim 1 further comprising a plurality of lockable wheels coupled to the station.

3. The integrated patient service center of claim 1 further comprising a table coupled to the station.

4. The integrated patient service center of claim 3 wherein the table is configured fold out from at least one off a side surface of the station.

5. The integrated patient service center of claim 3 wherein the table is configured fold out from at least a front surface of the station.

6. The integrated patient service center of claim 3 wherein the table has an adjustable height.

7. The integrated patient service center of claim 3 where the table comprises separate support leg(s) as long as things can be folded away/compact when not in use.

8. The integrated patient service center of claim 1 further comprising a privacy screen adapted to be drawn around the integrated patient service center to create a privacy space when rendering patient service.

9. The integrated patient service center of claim 8 wherein at least one portion of integrated patient service center is configured to extend above a height of the privacy screen, that would allow for branding visibility even when the privacy screen is drawn.

10. The integrated patient service center of claim 1 comprising at least one of the following: a printer, a touch-screen monitor, a non-touch monitor, a keyboard tray, a keyboard, a computer mouse, a USB Wifi Dongle, a Power Strip, a Surge Protector, a Scanner, a Collection Table, a Refrigerator, a Refrigerator Thermometer, a Supply Cabinet, a supply Drawer, or a Wifi Hotspot device.

11. The integrated patient service center of claim 1 the patient service center has a sharps container and a biohazard bin.

12. The integrated patient service center of claim 1 lockable cover is movable from a first position to a second position to close an opening that allows access to the user interface.

13. The integrated patient service center of claim 1 further comprising a controlled temperature storage unit that is lockable for storage of fluid samples obtained from the patient.

14. The integrated patient service center of claim 1 wherein the separate lockable access panel is on a side of the station to access the sample storage location.

15. The integrated patient service center of claim 1 wherein the separate lockable access panel is on a rear surface of the station to allow access to the sample storage location.

16. The integrated patient service center of claim 3 wherein the table comprises a thermal control areas to increase blood flow to a target area and thus increase the speed with which sufficient blood or other bodily fluid can be drawn from a subject.

17. The integrated patient service center of claim 16 the thermal control areas are configured to heat a target tissue to about 40° C. to 50° C.

18. The integrated patient service center of claim 16 the thermal control areas are configured to heat a temperature range of about 44° C. to 47° C.

19. An integrated patient service center comprising:
- a station having a lockable cover securing at least one portion of the station;
- a user accommodation section of the station adapted to locate a user in at least one position that enables an interaction between the station and the user;
- a user interface adapted to permit a user to input data relevant to the user; wherein said at least one position enables the user to position a portion of their body onto a work surface for obtaining patient service; and
- a secured, temperature controlled sample storage location that is configured to be accessible through a first opening and a second opening, wherein a key, code, or structure to open one opening does not open another opening.

* * * * *